United States Patent
Sato et al.

(10) Patent No.: US 7,700,106 B2
(45) Date of Patent: Apr. 20, 2010

(54) THERAPEUTIC AGENT FOR ULCERATIVE COLITIS

(75) Inventors: Nobuhiro Sato, 2-43-17-103, Ogikubo, Suginami-Ku, Tokyo (JP); Toshifumi Okusa, Tokyo (JP); Isao Okayasu, Sagamihara (JP)

(73) Assignees: Nobuhiro Sato, Tokyo (JP); Wakamoto Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 11/734,480

(22) Filed: Apr. 12, 2007

(65) Prior Publication Data

US 2007/0196931 A1  Aug. 23, 2007

Related U.S. Application Data

(63) Continuation of application No. 11/284,933, filed on Nov. 23, 2005, now abandoned, which is a continuation of application No. 09/931,951, filed on Aug. 20, 2001, now abandoned.

(30) Foreign Application Priority Data

Jun. 7, 2001  (JP)  ............................. 2001-172189

(51) Int. Cl.
*A61K 39/38* (2006.01)
*A61K 39/02* (2006.01)
*C12Q 1/00* (2006.01)
*G01N 33/53* (2006.01)
*A01N 37/18* (2006.01)

(52) U.S. Cl. ..................... 424/184.1; 424/234.1; 435/4; 435/7.1; 435/7.2

(58) Field of Classification Search ........................ None
See application file for complete search history.

(56) References Cited

OTHER PUBLICATIONS

Sartor (Gasreoenterology Clinic of North America (United States), Sep. 1995, 24, p. 475-507).*
Braegger (Acta Paediatr Suppl. 395: 18021, 1994).*
Fox et al (Infection and Immunity, Apr. 1999, p. 1757-1762).*
Macpherson et al (Gut, 1996,38:365-375).*
Coleman et al, (Applied and Environmental Microbiology, Oct. 1996, p. 3632-3639).*
Marx et al (Infection and Immunity, Jun. 1982, 36 (3) p. 943-948).*
Ushijima et al (Journal of Medical Microbiology, Sep. 1990, 33 (10:17-22).*
Sartor, Gasreoenterology Clinic of North America (United States), Sep. 1995, 24, pp. 475-507.
Danielsson et al., Scandinavian Journal of Infectious Diseases, 1979 (19), pp. 52-60.
Braegger, Acta Paediatr Suppl. 395: 18-21, 1994.
Fox et al, Infection and Immunity, Apr. 1999, pp. 1757-1762.
Marx et al, Infection and Immunity, Jun. 1982, 36 (3), pp. 943-948.
Macpherson et aI, Gut, 1996, 38: 365-375.
Coleman et al, Applied and Experimental Microbiology, Oct. 1996, pp. 3632-3639.
Ushijima et al, Journal of Medical Microbiology, Sep. 1990, 33(10): 17-22.
Onderdonk et al, Infection and Immunity, Jan. 1976, 13(10).
Dragstedt, Diseases of the colon and rectum (United States) Aug. 1988, 31 (8), pp. 658-664.
Ohkusa et al, Journal of Gastroenterology and Hepatology, 2002, 17, 849-853.

* cited by examiner

*Primary Examiner*—Vanessa L. Ford
(74) *Attorney, Agent, or Firm*—Oblon, Spivak, McClelland, Maier & Neustadt, L.L.P.

(57) ABSTRACT

Disclosed are pharmaceutical compositions of treatment for a patient with ulcerative colitis comprising a drug which can selectively kill *Fusobacterium varium* cells, or a drug which can neutralize the toxin produced by *Fusobacterium varium* cells, a method for screening such a drug, a method for treating a patient with the disease, a vaccine for the disease, a diagnostic drug, a diagnostic method, an experimental model for the disease and an experimental animal for the disease.

6 Claims, No Drawings

THERAPEUTIC AGENT FOR ULCERATIVE COLITIS

CROSS-REFERENCE TO RELATED APPLICATIONS

The present application is a continuation of U.S. Ser. No. 11/284,933, filed on Nov. 23, 2005, which is a continuation of U.S. Ser. No. 09/931,951, filed on Aug. 20, 2001, which claims priority to JP 2001-172189, filed on Jun. 7, 2001.

BACKGROUND OF THE INVENTION

The present invention relates to a drug for treating a patient with ulcerative colitis, which is one of the intractable diseases of unknown origin, a method for screening such a drug, a method for treating a patient with the disease, a prophylactic drug, a method for preventing such a disease, a vaccine for the disease, a diagnostic drug, a diagnostic method, an experimental model for the disease and an experimental animal for the disease.

Ulcerative colitis is one of the intractable diseases of digestive tracts and a unknown etiology. It has conventionally been regarded as an advantageous opinion that the ulcerative colitis would be a kind of autoimmune disease. For this reason, there have been used, for instance, steroid hormones, salazosulfapyridine and 5-ASA having an anti-inflammatory action. The administration of these drugs may clinically improve the symptoms of patients with this disease, but the disease recurs in most of cases, on a long term follow-up. Moreover, inflammatory findings still remain in both endoscopic and pathological findings in most of the cases of the disease, although the symptoms are improved. In other words, there has not yet been any drug for completely curing the disease.

SUMMARY OF THE INVENTION

Accordingly, it is an object of the present invention to provide a pharmaceutical composition for curing a patient with ulcerative colitis by eradication of Fusobacterium varium (F. varium).

It is another object of the present invention to provide a method for screening a drug and treatment having an effect of eradication of F. varium and treating ulcerative colitis, a method for treating a patient with ulcerative colitis, a prophylactic drug for the disease with F. varium infection, a method for preventing an infection with Fusobacterium varium, a vaccine for the disease, an agent and a method for diagnosing the infection with the bacterium, and an experimental model and an experimental animal for the disease.

The present inventors have examined patients with ulcerative colitis, and found that Fusobacterium varium cells are adhered to mucosa and invade into the mucus and ulcerative mucosa at high rates, the detection rate and value of the serum to the bacterium antibody is high, the amount thereof is large as compared with those observed for normal persons and patients suffering from other intestinal diseases and that the colic ulcer is caused due to butyric acid which is found to be produced by Fusobacterium varium. The F. varium itself has not been recognized to have any pathogenicity and have thus completed the present invention on the basis of the foregoing findings.

Accordingly, the present invention provides a pharmaceutical composition for treating a patient with ulcerative colitis, which comprises a drug capable of selectively killing Fusobacterium varium.

The present invention also provides a pharmaceutical composition for treating a patient with ulcerative colitis comprising a drug which can neutralize the toxin produced by Fusobacterium varium, a drug which can inhibit the adhesion of Fusobacterium varium to the intestinal mucosa or a drug which can inhibit the invasion of Fusobacterium varium into the intestinal mucosa as well as a vaccine for preventing ulcerative colitis comprising either of the foregoing drugs in an amount sufficient for preventing F. varium infection.

The present invention likewise provides a method for screening a drug for selectively killing Fusobacterium varium, which comprises the step of administering a candidate drug in an experimental model of Fusobacterium varium-infection to thus select a drug capable of selectively killing the bacterium.

The present invention also provides a method for screening a therapeutic agent for ulcerative colitis, which comprises the step of administering a candidate drug capable of selectively killing the bacterium to a patient suffering from ulcerative colitis and positive to Fusobacterium varium to thus select a drug capable of improving the symptoms of the patients with the disease.

Although F. varium as commersal bacteria has not been recognized to be pathogenic, we found that colonic ulcers indued by enema of butyric acid which was produced by the bacterium.

The present invention provides an animal as a model of ulcerative colitis obtained by administering a toxin produced by Fusobacterium varium to an animal.

The present invention also provides an animal as a model for ulcerative colitis comprising Fusobacterium varium cells adhered to the intestinal mucosa.

The present invention also provides a method for diagnosing ulcerative colitis comprising the step of detecting an antibody against Fusobacterium varium.

The present invention further provides an agent for making a diagnosis of ulcerative colitis comprising an antibody, which has the highest detection sensitivity and the highest specificity, among a plurality of antibodies against Fusobacterium varium.

DESCRIPTION OF THE PREFERRED EMBODIMENTS

Fusobacterium varium is a bacterium belonging to the genus Fusobacterium of the family Bacteroidaceae and was detected from the mucosa of a patient with ulcerative colitis at the active phase by bacterial cell culture and immunostaining. The rates of these detections were significantly higher than those observed for patients with ulcerative colitis at the remission stage, Crohn's disease, ischemic colitis, and colomic adenoma. Therefore, this bacterium is considered to be a causal bacterium or an exacerbation factor. From such information, it would be concluded that the patients with ulcerative colitis could be cured by administering a drug selectively killing this bacterium or an antimicrobial agent to remove the bacterial cells from the mucosa in the lesions. More specifically, there can be used antimicrobial agents having high susceptibility to Fusobacterium varium, such as tetracycline, penicillin, MNZ, imipenem, amoxicillin, cefmetazole, ampicillin, fosfomycin and chloramphenicol.

It has been recognized that the toxins produced by Fusobacterium varium cells have toxicity to vero cells. Therefore, the toxins were analyzed and it was found that they were organic acids produced by Fusobacterium varium and that the principal component thereof was identified to be butyric acid. Thus, when butyric acid was injected into the rectum of a mouse, a lesion similar to ulcerative colitis was induced. Accordingly, if administering a drug, which can neutralize and/or adsorb the butyric acid to a patient, the development of any lesion may be prevented or such conditions may be treated. Specifically, an agent for adsorbing organic acids such as activated carbon can be employed.

Since *Fusobacterium varium* cells are adhered to the surface mucosa of active ulcerative colitis, the crisis of ulcerative colitis can be prevented by inhibiting the adhesion of *Fusobacterium varium* cells to the affected mucosa even if *Fusobacterium varium* cells are present in the intestinal flora. Specifically, a drug for protecting mucosa such as sucralfate and ecabe sodium can be used.

As an evidence that *Fusobacterium varium* cells invade from digestive tracts into the intestinal mucosa, an antibody (serum antibody) against *Fusobacterium varium* is detected in the sera of the patients with ulcerative colitis in a high detection rate and high antibody titers by the ELISA assay. There has recently been elucidated the invasion mechanism of various kinds of bacteria into mucosa. Bacteria act on the mucosal cells by themselves to thus make the cells produce receptors and then they invade into the cells. *Fusobacterium varium* cells may possess the same function. Moreover, it would be considered that if *Fusobacterium varium* cells invade into the mucosa, macrophages can be activated and they may be involved in the crisis and exacerbation of inflammation. Therefore, the inflammation can be controlled by blocking the process of the bacterial invasion into the mucosa.

If a vaccine against *Fusobacterium varium* is developed, it would be possible to immediately eliminate *Fusobacterium varium* cells even if infected therewith and to prevent any crisis of ulcerative colitis or to inhibit the exacerbation of the symptoms, as in the case where the infection with pneumococcus can be inhibited by the vaccination with a pneumococcal vaccine.

A target drug can be screened by establishing an experimental infection model using a sterilized animal or a small animal in which *Fusobacterium varium* cells are adhered to the colonic mucosa. In these animals, a candidate drug administered to the experimental animal, can be evaluated whether the candidate drug can selectively kill *Fusobacterium varium* cells or not, by the culture, immunostaining and the serum antibody titer.

Patients with ulcerative colitis infected with *Fusobacterium varium* with are identified by diagnosing patients suffering from ulcerative colitis through the determination of the serum antibody titers, the cultivation of the mucosa or the immunostaining of affected mucosa, and then a candidate drug capable of selectively king *Fusobacterium varium* is administered to the patients after obtaining the informed consent of patients. Thus, the effectiveness of the drug as a therapeutic agent for ulcerative colitis can be evaluated by the symptoms of the ulcerative colitis are, in fact, improved or not and by investigating the presence of side effects and safety of the drug.

Moreover, the principal component of the toxin against the vero cells produced by *Fusobacterium varium* is found to be butyric acid, and butyric acid is injected into the colon of a small animal such as a mouse or a rat to thus establish a lesion similar to ulcerative colitis.

*Fusobacterium varium* cells are inoculated to germ-free animal or an compromised small animal and adhere the bacterial cells to the colonic mucosa. Moreover, it is also possible to find out animals highly sensitive to the adhesion of living bacterial cells to the intestinal mucosa by the inoculation of *Fusobacterium varium* cells into a variety of animals. Thus, an ulcerative colitis-like lesion can be developed or established in these animals and the establishment of such a lesion in the animals or the infection thereof with *Fusobacterium varium* can be judged on the basis of the results of the detection of the serum antibody, the immunostaining of mucosa and culture of the mucosa.

If the antibodies are identified by a method such as the western blot technique and/or an ELISA technique, a differential diagnosis as ulcerative colitis can be easily made as to the cases of inflammatory bowel disease, if the diagnosis is difficult.

The antibody detected by the western blot technique are separated and purified depending on the molecular weights of the components to thus identify or select a component of the antibody having the highest sensitivity to detection and the highest specificity and thus a diagnostic test for ulcerative colitis can be put on the market.

The pharmaceutical composition of treatment for ulcerative colitis according to the present invention comprises a drug capable of selectively killing *Fusobacterium varium*, a drug, which can neutralize the toxin produced by *Fusobacterium varium*, a drug, which can inhibit the adhesion of *Fusobacterium varium* to the mucosa or a drug, which can inhibit the invasion of *Fusobacterium varium* present into the mucosa, alone or in any combination with a variety of other additives. The resulting composition is thus ready for administrating to a patient with ulcerative colitis and positive to infection with *Fusobacterium varium*. Examples of the dosage forms of such a pharmaceutical composition include tablets, powders, pills, granules, capsules, suppositories, solutions, sugar-coated tablets, depots, or syrups. These dosage forms may be prepared by the use of currently used pharmaceutical auxiliary agents according to the usual methods. In this case, the pharmaceutical compositions preferably comprise pharmaceutically acceptable carriers and/or diluents in addition to the foregoing drugs.

For instance, a tablet can be prepared by admixing one of the foregoing drugs with known auxiliary agents. Examples of such auxiliary agents are inert diluents such as milk sugar, calcium carbonate or calcium phosphate; binders such as gum arabic, corn starch or gelatin; swelling agents such as alginic acid, corn starch or pre-gelatinized starch; sweeteners such as cane sugar, milk sugar or saccharin; perfumes such as peppermint oil, AKAMONO oil or cherry extract; lubricating and wetting agents such as magnesium stearate, talc or carboxymethyl cellulose; excipients for soft gelatin capsules and suppositories such as fats, waxes, semi-solid and liquid polyol, natural oils or hardened oils; and vehicles for solutions such as water, alcohol, glycerol, polyol, sucrose, invert sugar, glucose, vegetable oils.

The dose of the pharmaceutical composition used for the achievement of the foregoing objects is in general determined while taking into consideration various factors such as intended therapeutic effects, routes of administration, terms required for the treatment, and ages and body weights of patients to be treated, but the dose for adult preferably ranges from 1 µg to 5 g per day for the administration through the oral route and 0.01 µg to 1 g per day for the administration through the parenteral route.

The present invention will further be described with reference to the following Examples in more detail. These Examples simply illustrate preferred embodiments of the present invention and so the present invention is not restricted to these specific Examples at all.

EXAMPLE 1

Biopsy specimens from patients with active UC were cultured aerobically and anaerobically. Bacteria with filtered culture supernatants cytotoxic to Vero cells were examined by PCR for verotoxin genes. HPLC was performed with culture supernatants of cytotoxic strains for organic acid concentrations. Mice were given enemas containing organic acid at mean concentration in the supernatants of cytotoxic strains to ascertain whether colonic lesions resembling those of UC appeared. We further investigated sera of patients with UC for antibodies against cytotoxic bacteria by western blotting and enzyme-linked immunosorbent assays (ELISA), and examined biopsied mucosa for these bacteria by immunohistochemistry. Only strains of *Fusobacterium varium* (*F. varium*) isolated killed Vero cells. The bacterium lacks verotoxin genes but culture supernatant was found to contain much butyric acid. Twenty-four hours after enemas containing butyric acid or *F. varium* culture supernatants, mice demonstrated colonic ulcers with crypt abscesses, inflammatory cell infiltration and apoptotic changes. Western blotting with *F. varium* showed 19 of 31 (61%) patients to have serum antibodies to the bacterium. In ELIZA and immunohistochemistry with *F. varium* proteins an antigen, the mean optical density and the detection rate were higher for our patients than for subjects with Crohn's disease or other controls.

EXAMPLE 2

The susceptibility to *Fusobacterium varium* in antimicrobial agents was examined. As a result, *Fusobacterium varium* was found to be susceptibility to the following antimicrobial agents in the order indicated: tetracycline>penicillin>MNZ>imipenem>amoxicillin, cefmetazole, ampicillin, fosfomycin, chloramphenicol. On the other hand, the bacterium was found to be resistant to clarithromycin, erythromycin, streptomycin, kanamycin and gentamycin.

What is claimed is:

1. A method for determining the probability of a patient developing or having ulcerative colitis caused by *Fusobacterium varium*, which comprises: (a) obtaining sera from said patient; (b) detecting an antibody for *Fusobacterium varium* in said sera; and (c) preliminarily determining that the probability for developing or having ulcerative colitis is high in said patient if the antibody is detected.

2. The method of claim 1, wherein said antibody is detected using western blotting method.

3. The method of claim 1, wherein said antibody is detected using enzyme-linked immunosorbent assay (ELISA).

4. A method for identifying a patient as having ulcerative colitis caused by *Fusobacterium varium*, which comprises: (a) obtaining sera from said patient; (b) detecting an antibody for *Fusobacterium varium* in said sera; and (c) identifying said patient as suffering from ulcerative colitis if the amount of antibody detected is significantly greater than a threshold value predetermined in healthy controls and Crohn's disease.

5. The method of claim 4, wherein said antibody is detected using western blotting method.

6. The method of claim 4, wherein said antibody is detected using enzyme-linked immunosorbent assay (ELISA).

* * * * *